United States Patent [19]

Chang et al.

[11] Patent Number: 5,650,531
[45] Date of Patent: Jul. 22, 1997

[54] HIGHLY PENDANT PHOSPHORUS-CONTAINING REACTIVE OLIGOMER FLAME RETARDANT

[75] Inventors: Shinn-Jen Chang, Hsinchu; Yuung-Ching Sheen, Tainan Hsien; Yi-Ni Cheng, Taipei; Rong-Shuh Chang, Hsinchu, all of Taiwan

[73] Assignee: Industrial Technology Research Institute, Hsinchu, Taiwan

[21] Appl. No.: 496,174

[22] Filed: Jun. 28, 1995

[51] Int. Cl.$^6$ .................................. C07F 9/32; C07F 9/40
[52] U.S. Cl. .................................. 558/160; 558/180
[58] Field of Search ........................... 558/160, 180

[56] References Cited

U.S. PATENT DOCUMENTS 3,376,274 4/1968 Boyer et al. .................. 558/180 X

*Primary Examiner*—Johann Richter
*Assistant Examiner*—Michael G. Ambrose
*Attorney, Agent, or Firm*—Sughrue, Mion, Zinn, Macpeak & Seas

[57] ABSTRACT

The synthesis of a non-halogen flame retardant oligomer containing highly pendnat phosphorus moieties is disclosed. Diols, unsaturated double bond-containing dicarboxylic acids or acid anhydrides and saturated dicarboxylic acids or acid anhydrides are first esterified to form an oligomeric unsaturated polyester, and then a phsophorus-containing compound is grafted onto the oligomeric unsaturated polyester through addtion reaction in the presence of a selected metal complex catalyst.

20 Claims, No Drawings

1

HIGHLY PENDANT PHOSPHORUS-CONTAINING REACTIVE OLIGOMER FLAME RETARDANT

BACKGROUND OF THE INVENTION

1. Field of the Invention

The present invention relates to the synthesis of a non-halogen flame retardant oligomer containing highly pendant phosphorus moities. In particular, it relates to a process for preparing the flame retardant oligomer including first forming a polyester oligomer, and then grafting a phosphorus-containing compound onto the oligomer through an addition reaction.

2. Description of the Prior Art

Flame retardant and heat resistant polymeric materials can be obtained by polymer modification. This modification method involves reacting the flame retardant monomers onto the polymeric backbones by copolymerization. Because the flame retardant monomers are chemically bonded to the polymeric backbones, they will not migrate to the surface of the polymeric resins during processing such as extruding or injecting molding, and thus physical properties and flame retardancy are not affected. Moreover, when the thus obtained polymeric materials are woven into fabrics or are formed into nonwoven fabrics, they display good washing fastness and permanent flame retardancy. However, the process of copolymerization is complicated.

To obtain flame retardancy, an easier way is to coat a layer of a flame retardant on fabricated articles of polymeric resins. This method has the advantage of easy treatment. However, this method also has the disadvantages that only the surface of the fabricated articles are flame retardant and when they are formed into fabrics, the flame retardancy will gradually diminish with repeated washings. That is, the washing fastness of the thus treated fabrics is unsatisfactory.

Blending flame retardants with polymeric resins is the most convenient way to obtain flame retardant polymeric materials. However, organic flame retardants usually can not withstand processing at an elevated temperature, and therefore a lot of organic flame retardants in the blend is lost due to decomposition. In addition, poor compatibility between polymers and flame retardants often cause the migration of flame retardants when the blend is processed or used.

Recently, phosphorus-containing and high molecular weight flame retardants have been developed to replace conventional halogen-containing flame retardants to meet the requirements of low toxicity, low smoke and low migration in view of environment protection and public safety. For example, CR733 of Daihachi Chemical Industry Co., Ltd. Japan, and RDP and Fyrol of AKZO Co., Ltd. are phosphate flame retardants having a molecular weight of less than 2000. These kinds of phosphorus-containing flame retardants are usually synthesized by first reacting phosphorus-containing compounds with unsaturated diacids at a temperature of 150° C. for about 4 hours to form phosphorus-containing comonomers, and then reacting the phosphorus-containing monomers with saturated dicarboxyl acids and diols at an elevated temperature for example, 180°–200° C. to form the final products. The second step of this synthesis usually lasts for about 9–11 hours, which means a total synthesis time of 13–15 hours. Because the phosphorus-containing comonomers are subjected a lengthened period of reaction, they decompose, and then migrate during the reaction. Thus the final products have poor heat resistance and low phosphorus content, and are deeply colored, usually brown in color..

SUMMARY OF THE INVENTION

It is an object of the invention to provide a reactive, high phosphorus content, heat resistant and uncolored flame retardant which is prepared by a relatively short reaction process in which the phosphorus-containing compound is not decomposed and does not migrate.

To attain the above object of the invention, the process of the invention includes first esterifing diols with unsaturated double bond-containing dicarboxylic acid or acid anhydride or a derivative thereof, a saturated dicarboxylic acid or acid anhydride to form an oligomeric unsaturated polyester, and then in the presence of a properly selected, highly efficient catalyst, grafting a phosphorus-containing compound through an addition reaction to the oligomeric unsaturated polyester.

According to an aspect of the invention, a highly efficient catalyst is a metal complex catalyst represented by formula $MX_4$ or $H_2MX_6$ where M is a metal of Group VIII of the periodic table and X is a halogen or a compound of S, O or Si.

According to another aspect of the invention, the esterification is conducted at 155° C.–260° C. for 6–7 hours and the addition reaction is conducted at 100° C.–125° C. for 3–4 hours.

According to a further aspect of the invention, the esterification is conducted in the presence of a double bond polymerization inhibitor such as quinone.

According to yet a further aspect of the invention, the resulting flame retardants are uncolored highly pendant phosphorus-containing oligomeric flame retardants having a molecular weight up to 5000, a phosphorus content up to 9.5 wt %, a thermal decomposition temperature higher than 350° C., a weigh loss (280° C., under $N_2$ gas) less than 1%. These phosphorus-containing oligomeric flame retardants are reactive, and thus in addition to use as general flame retardant additives, they can react with —NCO, —COOH and —$NH_2$ groups to chemically bond to polymeric backbones to provide polymers, such as polyvinyl alcohols, ethylene vinyl acetates (EVA), polyurethanes, unsaturated polyesters, and phenolic resins with good physical properties and flame retardancy. The flame retardant oligomers of the invention can also be emulsified with water to form emulsified flame retardants to be added in aqueous resins such as EVA or acrylic resins.

The present invention can be more fully understood by reference to the following detailed descriptions.

DETAILED DESCRIPTION OF THE INVENTION

The phosphorus-containing compounds suitable for use in invention are those having the formula:

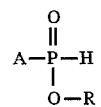

wherein A is —R or —OR where R is a $C_1$–$C_{10}$ alkyl group or a substituted or group usually phenyl, naphthyl, and biphenyl.

Unsaturated double bond-containing dicarboxylic acids or acid anhydrides or the derivatives thereof suitable for use in the invention include but are not limited to maleic acid, maleic anhydride, fumaric acid, iraconic acid, citraconic acid, mesaconic acid, and aconic acid.

Saturated dicarboxylic acid anhydrides suitable for use in the invention include but are not limited to adipic acid, sebacic acid, azelaic acid, docecane dicarboxylic acid, diesters of these acids, and the mixtures thereof.

Diols suitable for use in the invention include but are not limited to ethylene glycol, 1,4-butane diol, 1,6-hexanediol, diethylene glycol and the mixtures thereof.

The Examples of metal complexes suitable for use in the addition reaction include but are not limited to $PtCl_4$, $NiCl_4$, $PdCl_4$ and siloxane of Pt, such as platinum divinyl tetramethyldisiloxane, or platinum cyclovinyl methyl siloxane. These metal complexes can be used singly or as their mixtures. The amount of the metal complex added is 0.003–0.040 percent by weight based on the total amount of the oligomeric polyester and the phosphorus-containing compound.

According to the invention, the esterification is conducted in the presence of a protonic acid in combination with a metal compound of a Lewis acid serving as a catalyst. Examples of proton acids include but are not limited to para-toluene sulfonic acid (PTSA), hydrochloric acid, sulfuric acid, acetic acid, phosphoric acid, and pehenyl sulfonic acid. Metal compounds of Lewis acids include but are not limited to zinc acetate, manganous acetate, calcium acetate, tin oxide, antimony oxide, zinc oxide, tin oxide and germanium oxide. The protonic acids and the metal compounds of lewis acids are combined in a molar ratio of from 2:3 to 1:1.

To inhibit the self-polymerization of the unsaturated dicarboxylic acids, it is necessary for the invention to add a double bond polymerization inhibitor, for example, a quinone, such as hydroquinone, butyl quinone, dibutyl hydroquinone, methyl hydroquinone, in the esterification process. The amount of the inhibitors is usually 500–3000 ppm based on the total charge.

The esterification is conducted by adding double bond polymerization inhibitors, unsaturated double bond-containing dicarboxylic acids or acid anhydrides or derivatives thereof, saturated dicarboxylic acids or acid anhydrides, diols and protonic acid combined metal compounds of Lewis acids in one reactor and reacting at 155° C.–260° C., preferably 160° C.–230° C. The molar ratio of diol to total diacid is 1.03:1.0 to 5.0:1.0. After the conversion reaches 95%, the reactor is evacuated with a vacuum pump to 10 mmHg within 40 minutes. To the unsaturated polyester oligomer obtained is then added the phosphorus-containing compounds and the metal complexes, and reacted at 90°–120° C. to graft the phsophorus-containing compound onto the polyester oligomers. The molar ratio of the phosphorus-containing compound to the unsaturated dicarboxylic acid is 1:1.

The flame retardant polyester oligomers thus prepared have the structure:

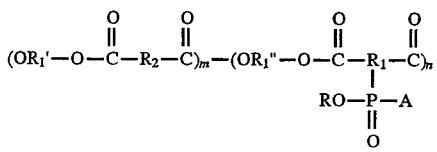

wherein $R_1'$, $R_1''$, $R_1$, and $R_2$ are respectively a $C_2$–$C_{12}$ alkylene group or a substituted or unsubstituted phenylene, group R is a $C_1$–$C_{10}$ alkyl group or a substituted or unsubstituted phenyl, group m is an integer of 1–14. These and n is an integer of 1–14, said flame retardant polyester oligomers have a molecular weight of 400–5000.

The invention is more specifically described by the following illustrative examples. In these examples, the phosphorus contents were obtained by heating samples in a mixture of sulfuric acid and perchloric acid to decompose, developing their colors by using ammonium molybdate and ammonium ferric sulfate, and measuring the color by a colormetric a method. The acid values were obtained by dissolving samples in a ½ solvent mixture of phenol and chloroform, and titrated with 0.1N KOH/phenyl alcohol solution using phenol red as an indicator. The percent of phosphorus incorporated into the polyester oligomer backbones was confirmed and measured by using $^{31}$P-NMR. Self extinguish was measured in accordance with ASTM D2863.

EXAMPLE 1

164.3 g of adipic acid(AA), 48.8 g of iraconic acid, 120.9 g of ethylene glycol (EG), 0.11 g of hydroquinone, 0.09 g of PTSA and 0.12 g of TBT (tetra(butylorthotitante)) were added to a 1.5 liter stainless reactor fitted with a fractionating column, a stirrer, and a nitrogen gas inlet and, heated to a temperature of 175°–185° C. and maintained for esterification. When the conversion reached 95%, the reactor was evacuated to a pressure of 10 mm Hg within 40 minutes, and maintained at this pressure for 1 hour to obtain a polyester oligomer. 0.024 g of $PtCl_4$, 81 g of [1.2] oxaphosphorin-6-yl methyl butanedioic acid (DOP) were then added to the reaction system and reacted at 115° C. for 3 hours to yield a polyester oligomer. The polyester oligomer had an acid value of 2.0 mg/g, and a molecular weight of 4200. The conversion was 98%, and the phosphorus content was 3.43%. Other properties of the polyester oligomer obtained are summarized in Table 1.

EXAMPLE 2

87.6 g of adipic acid(AA), 78 g of itaconic acid, 119 g of ethylene glycol (EG), 0.16 g of butyl quinone (BQ), 0.12 g of RSnO, and 0.08 g of PTSA were added to a 1.5 liter stainless reactor fitted with a fractionating column, stirrer, and nitrogen gas inlet, heated to a temperature of 175°–185° C. and maintained for esterification. When the coversion reached 98%, the reactor was evacuated to a pressure of 10 mm Hg within 40 minutes, and maintained at this pressure for 1 hour to obtain a polyester oligomer. 0.023 g of $PtBr_4$, 129.6 g of DOP were then added to the reaction system and reacted at 105° C. for 3 hours to yield a polyester oligomer. The polyester oligomer had an acid value of 2.4 mg/g, and a molecular weight of 3900. The conversion was 93%, and the phosphorus content was 5.3%. Other properties of the polyester oligomer obtained are summarized in Table 1.

EXAMPLE 3

39 g of adipic acid(AA), 117 g of itaconic acid, 148.8 g of ethylene glycol (EG), 0.18 g of dibutyl hydroquinone (DBHQ), 0.14 g of Sn(oxalate), and 0.094 g of PTSA were added to a 1.5 liter stainless reactor fitted with a fractionating column, stirrer, and a nitrogen gas inlet, heated to a temperature of 195°–205° C. and maintained for esterification. When the conversion reached 96%, the reactor was evacuated to a pressure of 10 mmHg within 40 minutes, and maintained at this pressure for 1 hour to obtain a polyester oligomer. 0.035 g of $H_2PtCl_6$, 194.4 g of DOP were then added to the reaction system and reacted at 110° C. for 3 hours to yield a polyester oligomer. The polyester oligomer had an acid value of 2.3 mg/g, and a molecular weight of 4100. The conversion was 93%, and the phosphorus content was 6.7%. Other properties of the polyester oligomer obtained are summarized in Table 1.

EXAMPLE 4

156 g of itaconic acid, 148.8 g of ethylene glycol (EG), 0.156 g of methyl hydroquinone (MEHQ), 0.15 g of TBT, and 0.15 g of PTSA were added to a 1.5 liter stainless reactor fitted with a fractionating column, stirrer, and nitrogen gas inlet, heated to a temperature of 185°–195° C. and maintained for esterification. When the conversion reached 98%, the reactor was evacuated to a pressure of 10 mm Hg within 40 minutes, and maintained at this pressure for 1 hour to obtain a polyester oligomer. 0.039 g of $PtCl_4$, 259.2 g of DOP were then added to the reaction system and reacted at 110° C. for 3 hours to yield a polyester oligomer. The polyester oligomer had an acid value of 2.1 mg/g, and a molecular weight of 3600. The conversion was 90.3%, and the phosphorus content was 7.5%. Other properties of the polyester oligomer obtained are summarized in Table 1.

EXAMPLE 5

117.6 g of maleic anhydride, 148.8 g of ethylene glycol (EG), 0.117 g of methyl hydroquinone (MEHQ), 0.12 g of RSnO, and 0.10 g of PTSA were added to a 1.5 liter stainless reactor fitted with a fractionating column, stirrer, and nitrogen gas inlet, heated to a temperature of 175°–185° C. and maintained for esterification. When the conversion reached 96%, the reactor was evacuated to a pressure of 10 mm Hg within 40 minutes, and maintained at this pressure for 1 hour to obtain polyester oligomer. 0.059 g of $PtBr_4$, 259.2 g of DOP were then added to the reaction system and reacted at 115° C. for 3 hours to yield a polyester oligomer. The polyester oligomer had an acid value of 3.1 mg/g, and a molecular weight of 3400. The conversion was 91.8%, and the phosphorus content was 7.9%. Other properties of the polyester oligomer obtained are summarized in Table 1.

EXAMPLE 6

43.8 g of adipic acid, 156 g of iraconic acid, 93 g of ethylene glycol (EG), 135 g of butyl glycol, 0.19 g of methyl hydroquinone (MEHQ), 0.12 g of TBT, and 0.12 g of PTSA were added to a 1.5 liter stainless reactor fitted with a fractionating column, a stirrer, and a nitrogen gas inlet, heated to a temperature of 175°–185° C. and maintained for esterification. When the conversion reached 98%, the reactor was evacuated to a pressure of 10 mm Hg within 40 minutes, and maintained at this pressure for 1 hour to obtain a polyester oligomer. 0.031 g of $H_2PtBr_6$, 132 g of dimethyl phosphate were then added to the reaction system and reacted at 105° C. for 3 hours to yield a polyester oligomer. The polyester oligomer had an acid value of 3.4 mg/g, and a molecular weight of 3500. The conversion was 90.5%, and the phosphorus content was 8.6%. Other properties of the polyester oligomer obtained are summarized in Table 1.

EXAMPLE 7

43.8 g of adipic acid, 117.6 g of maleic anhydride, 139.5 g of ethylene glycol (EG), 46.5 g of butyl glycol, 0.16 g of methyl hydroquinone (MEHQ), 0.064 g of PTSA, and 0.096 g of TBT were added to a 1.5 liter stainless reactor fitted with a fractionating column, a stirrer, and a nitrogen gas inlet, heated to a temperature of 185°–195° C. and maintained for esterification. When the coversion reached 96%, the reactor was evacuated to a pressure of 10 mmHg within 40 minutes, and maintained at this pressure for 1 hour to obtain polyester oligomer. 0.035 g of $PtCl_4$, 166 g of diethyl phosphate were then added to the reaction system and reacted at 115° C. for 3 hours to yield a polyester oligomer. The polyester oligomer had an acid value of 3.6 mg/g, and a molecular weight of 4050. The conversion was 91.8%, and the phosphorus content was 8.6%. Other properties of the polyester oligomer obtained are summarized in Table 1.

EXAMPLE 8

43.8 g of adipic acid, 156 g of itaconic acid, 74.4 g of ethylene glycol (EG), 141.6 g of hexadiol, 0.12 g of Sn(oxalate), 0.19 g of methyl hydroquinone (MEHQ), and 0.12 g of PTSA were added to a 1.5 liter stainless reactor fitted with a fractionating column, a stirrer, and a nitrogen gas inlet, heated to a temperature of 175°–185° C. and maintained for esterification. When the conversion reached 96%, the reactor was evacuated to a pressure of 10 mm Hg within 40 minutes, and maintained at this pressure for 1 hour to obtain a polyester oligomer. 0.0312 g of $H_2PtBr_4$, 132 g of dimethyl phosphate were then added to the reaction system and reacted at 105° C. for 3 hours to yield a polyester oligomer. The polyester oligomer had an acid value of 2.6 mg/g, and a molecular weight of 5000. The conversion was 90%, and the phosphorus content was 8.1%. Other properties of the polyester oligomer obtained are summarized in Table 1.

EXAMPLE 9

156 g of itaconic acid, 74.4 g of ethylene glycol (EG), 108 g of butyl glycol, 0.07 g of PTSA, 0.086 g of TBT, and 0.0156 g of BQ were added to a 1.5 liter stainless reactor fitted with a fractionating column, a stirrer, and a nitrogen gas inlet, heated to a temperature of 195°–200° C. and maintained for esterification. When the conversion reached 98% the reactor was evacuated to a pressure of 10 mmHg within 40 minutes, and maintained at this pressure for 1 hour to obtain polyester oligomer. 0.031 g of $PtBr_4$, 259 g of DOP were then added to the reaction system and reacted at 100° C. for 3 hours to yield a polyester oligomer. The polyester oligomer had an acid value of 2.5 mg/g, and a molecular weight of 4700. The conversion was 95%, and the phosphorus content was 8.1%. Other properties of the polyester oligomer obtained are summarized in Table 1.

Comparative Example 1

156 g of itaconic acid and 259.2 g of DOP were added to a 1.5 liter stainless reactor fitted with a fractionating column, a stirrer, and a nitrogen gas inlet, heated to a temperature of 140° C. to form a phosphorus-containing diacid. 148.8 g of ethylene glycol was then added to the reaction system, and heated to 195° C. for esterification. The properties of the resulting product are summarized in Table 1.

Comparative Example 2

The same procedures and materials as in Comparative Example 2 were used, except itaconic acid was changed to maleic anhydride. The properties of the resulting product are summarized in Table 1.

Comparative Example 3

The same procedures and materials as in Example 6 were used, except no combined catalyst for esterification was added, only TBT was added. $H_2PtBr_6$ was also omitted. The properties of the resulting product are summarized in Table 1.

TABLE 1

| Example | Reaction Type | Metal Complex | Combined Catalyst | Phosphorus Content (%) | Phosphorus Conversion (%) | Molecular weight | Reaction Time (hr) | Reaction Temperature Polycondensation | Reaction Temperature Addition | Self-extinguishing |
|---|---|---|---|---|---|---|---|---|---|---|
| 1 | forming oligomeric polyester then grafting | $PtCl_4$ | yes | 3.41 | 98 | 4200 | 10 | 170 | 115 | o |
| 2 | forming oligomeric polyester then grafting | $PtBr_4$ | yes | 5.3 | 93 | 3900 | 9 | 170 | 105 | o |
| 3 | forming oligomeric polyester then grafting | $H_2PtCl_6$ | yes | 6.7 | 93 | 4100 | 10.5 | 175 | 110 | o |
| 4 | forming oligomeric polyester then grafting | $PtCl_4$ | yes | 7.5 | 90.3 | 3600 | 9.5 | 175 | 115 | o |
| 5 | forming oligomeric polyester then grafting | $PtBr_4$ | yes | 7.9 | 91.8 | 3400 | 10 | 170 | 115 | o |
| 6 | forming oligomeric polyester then grafting | $H_2PtBr_6$ | yes | 8.6 | 90.5 | 3500 | 10.5 | 175 | 105 | o |
| 7 | forming oligomeric polyester then grafting | $PtCl_4$ | yes | 8.6 | 91.8 | 4050 | 10.5 | 175 | 115 | o |
| 8 | forming oligomeric polyester then grafting | $H_2PtBr_6$ | yes | 8.1 | 90 | 4000 | 9.5 | 175 | 120 | o |
| 9 | forming oligomeric polyester then grafting | $PtBr_4$ | yes | 7.6 | 95 | 3700 | 10.5 | 175 | 105 | o |
| Comparative Example 1 | forming phosphorus-containing diacid, then esterifying | — | No | 6.6 | 79.5 | 400 | 14 | 195 | 155 | o |
| Comparative Example 2 | forming phosphorus-containing diacid, then esterifying | — | NO | 5.9 | 71 | 850 | 15 | 195 | 160 | o |
| Comparative Example 3 | forming oligomeric polyester then grafting | $PtCl_4$ | NO | 6.0 | 63 | 3500 | 13 | 195 | 105 | o |
| Comparative Example 4 | only polycondensing* | — | No | 0 | — | 4000 | 9 | 200 | — | X |

What is claimed is:

1. A process for preparing a flame retardant oligomer having the formula:

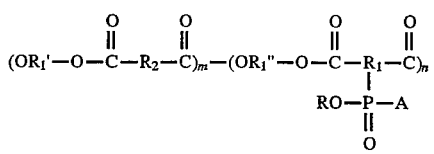

wherein $R_1'$, $R_1''$, $R_1$ and $R_2$ are respectively a $C_2$–$C_{12}$ alkylene group or a substituted or unsubstituted phenylene group, R is a $C_1$–$C_{10}$ alkyl group or a substituted or unsubstituted phenyl group, m is an integer of 1–14 and n is an integer of 1–14, comprising the following steps:

(a) in the presence of a double bond polymerization inhibitor, subjecting a double bond-containing unsaturated dicarboxylic acid, acid anhydride thereof or a derivative therof, a saturated dicarboxylic acid or an acid anhydride thereof, and a diol to esterification to form a polyester oligomer; and (b) in the presence of a metal complex catalyst, grafting a phosphorus-containing compound having the formula:

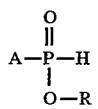

wherein A is —R or —OR where R is a $C_1$–$C_{10}$ alkyl group or a substituted or unsubstituted phenyl group through an addition reaction to said polyester oligomer.

2. The process as claimed in claim 1, wherein said metal complex catalyst is a complex represented by formula $MX_4$ or $H_2MX_6$ where M is a metal of Group VIII group of the periodic table and X is a halogen or a siloxane.

3. The process as claimed in claim 2, wherein said metal complex is a complex selected from the group consisting of $PtCl_4$, $NiCl_4$, $PdCl_4$ and a siloxane of Pt.

4. The process as claimed in claim 1, wherein the amount of said metal complex is 0.003–0.040 percent by weight based on the total amount of the oligomer and the phosphorus-containing compound.

5. The process as claimed in claim 4, wherein the amount of said metal complex is 0.005–0.015 percent by weight based on the total amount of the oligomer and the phosphorus-containing compound.

6. The process as claimed in claim 1, wherein said double bond-containing dicarboxylic acid or acid anhydride or the derivative thereof is selected from the group consisting of maleic acid, maleic anhydride, fumaric acid, itaconic acid, citraconic acid, mesaconic acid, and aconic acid.

7. The process as claimed in claim 1, wherein said saturated dicarboxylic acid or acid anhydride is selected from the group consisting of adipic acid, sebacic acid, azelaic acid, docecane dicarboxylic acid, a diester of these acids, and a mixture thereof.

8. The process as claimed in claim 1, wherein said diol is selected from the group consisting of ethylene glycol, 1,4-butane diol, 1,6-hexanediol, diethylene glycol and a mixture thereof.

9. The process as claimed in claim 1, wherein in the esterification reaction, the molar ratio of diol to diacid is 1.03:1.0 to 5.0:1.0, and the molar ratio of phosphorus-containing compound to double bond-containing dicarboxylic acid is 1:1.

10. The process as claimed in claim 1, wherein the esterification is conducted at 155° C.–260° C. for 6–7 hours.

11. The process as claimed in claim 10, wherein the esterification is conducted at a 160° C.–230° C.

12. The process as claimed in claim 1, wherein said addition reaction is conducted at a temperature of 90° C.–120° C. for 3–4 hours.

13. The process as claimed in claim 1, wherein the esterification is conducted in the presence of a proton acid in combination with a metal compound of a Lewis acid as a catalyst wherein the molar ratio of proton acid to metal compound is from 2:3 to 1:1.

14. The process as claimed in claim 13, wherein the proton acid catalyst is selected from the group consisting of para-toluene sulfonic acid, hydrochloric acid, sulfuric acid, acetic acid, phosphoric acid, and phenyl sulfonic acid.

15. The process as claimed in claim 13, wherein the metal compound of the Lewis acid is selected from the group consisting of zinc acetate, manganous acetate, calcium acetate, tin oxide, antimony oxide, zinc oxide, tin oxide and germanium oxide.

16. The process as claimed in claim 1, wherein said double bond polymerization inhibitor is a quinone.

17. The process as claimed in claim 16, wherein said quinone is selected form the group consisting of hydroquinone, butyl quinone, dibutyl hydroquinone and methyl hydroquinone.

18. The process as claimed in claim 1, wherein the amount of the double bond polymerization inhibitor is 500–3000 ppm based on the total charges.

19. A flame retardant oligomer having the formula:

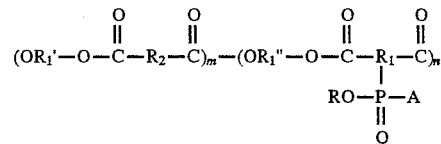

wherein $R_1'$, $R_1''$, $R_1$ and $R_2$ are respectively a $C_2$–$C_{12}$ alkylene group or a substituted or unsubstituted phenylene group, A is —R or —OR where R is a $C_1$–$C_{10}$ alkyl group or a substituted or unsubstituted phenyl group, m is an integer of 1–14 and n is an integer of 1–14.

20. The flame retardant oligomer as claimed in claim 19, having a molecular weight of 400–5000.

* * * * *